United States Patent [19]

Krespan

[11] Patent Number: 5,185,477
[45] Date of Patent: Feb. 9, 1993

[54] HALOHYDRIN COMMPOUNDS

[75] Inventor: Carl G. Krespan, Wilmington, Del.

[73] Assignee: E. I. du Pont de Nemours and Company, Wilmington, Del.

[21] Appl. No.: 803,441

[22] Filed: Dec. 6, 1991

Related U.S. Application Data

[62] Division of Ser. No. 448,651, Dec. 11, 1989, Pat. No. 5,101,058.

[51] Int. Cl.$^5$ .................... C07C 31/34; C07C 41/00
[52] U.S. Cl. .................... 568/842; 568/677
[58] Field of Search ................ 568/842, 677

[56] References Cited

U.S. PATENT DOCUMENTS

| | | | |
|---|---|---|---|
| 2,700,686 | 1/1955 | Dickey et al. | 260/633 |
| 3,562,310 | 2/1971 | Anello et al. | 260/457 |
| 4,362,672 | 12/1982 | Yamabe et al. | 260/544 |

FOREIGN PATENT DOCUMENTS

| | | |
|---|---|---|
| 1083031 | 3/1989 | Japan . |
| 1233243 | 9/1989 | Japan . |
| 390084 | 3/1974 | U.S.S.R. . |

OTHER PUBLICATIONS

C. G. Krespan and D. A. Dixon, J. Org. Chem., vol. 51, pp. 4460–4466 (1986).
C. Coudures et al., J. Fluorine Chem., vol. 24, pp. 93–104 (1984).
E. T. McBee et al., J. Am. Chem. Soc., vol. 74, pp. 3022–3023.
D. D. Smith, et al., Ind. Eng. Chem., vol. 49, pp. 1241–1246 (1957).

*Primary Examiner*—Marianne M. Cintins
*Assistant Examiner*—Rebecca Cook

[57] ABSTRACT

Novel fluorinated (poly)sulfates, halosulfonates, halohydrins and epoxides, as well as novel processes for producing them are disclosed.

7 Claims, No Drawings

HALOHYDRIN COMMPOUNDS

This is a division of Ser. No. 07/448,651, filed on Dec. 11, 1989. U.S. Pat. No. 5,101,058

FIELD OF THE INVENTION

Novel fluorinated halosulfonates, (poly)sulfates, halohydrins and epoxides, which are useful as monomers and chemical intermediates, are prepared by reacting (perfluoroalkyl)ethylenes with a combination of sulfur trioxide and a halogen, and further reacting the products of that reaction.

BACKGROUND OF THE INVENTION

U.S. Pat. No. 3,562,310 describes the preparation of compounds of the formula $[R(CH_2)_m]_2(OSO_2)_pO$ by the reaction of $R(CH_2)_mI$ with sulfur trioxide ($SO_3$), wherein m is 1, 2 or 3, p is an integer of 2 to 6, and R is perfluoroalkyl. The hydrolysis of these polysulfates to the corresponding alcohol is also described. No mention is made of the use of halogen with the $SO_3$, nor of the use of a fluorinated olefin in a reaction with $SO_3$.

U.S. Pat. No. 4,362,672 describes the preparation of difluorohaloacetyl fluoride by the reaction of $CF_2=CFY$ with $SO_3$ and bromine or iodine to produce an intermediate compound containing the group $XCF_2CFYOSO_2$— wherein X is I or Br and Y is F, Cl, Br or I. The difluorohaloacetyl fluoride is obtained by decomposing the intermediate thermally, optionally in the presence of catalysts. In this patent only fully halogenated (but otherwise unsubstituted) ethylenes are reacted. This is in contrast to the present invention where the (perfluoroalkyl)ethylenes that react with the $SO_3$/halogen combination contain no vinylic halogen.

C. G. Krespan and D. A. Dixon, J. Org. Chem., Vol. 51, pp. 4460-4466 (1986) describe the reaction of $SO_3$ with perfluoro-2-butene. In this paper the olefin is fully fluorinated and no halogen is used in combination with the $SO_3$.

Two publications describe the preparation of halohydrins of mono(perfluoroalkyl)ethylenes, and (usually) their subsequent reaction with base to form the corresponding epoxides. Reaction of the mono(perfluoroalkyl)ethylenes with hypohalous acids (U.S. Pat. No. 2,700,686), or with bromine and acetic acid in the presence of mercuric ion [C. Coudures, et al., J. Fluorine Chem., Vol. 24, pp. 93-104 (1984)] are methods of making the mono(perfluoroalkyl)ethylene halohydrins. Other publications such as U.S.S.R. Patent 390,084 [Chem. Abs., Vol. 80, 27084u (1974)] and E. T. McBee and T. M. Burton, J. Am. Chem. Soc., Vol. 74, pp, 3022-3023 (1952) describe the preparation of the halohydrins and epoxides of mono(perfluoroalkyl)ethylenes by other methods. A short "review" of early work on forming epoxides nominally derived from mono(perfluoroalkyl)ethylenes is found in D. D. Smith, et al., Ind. Eng. Chem., Vol. 49, pp. 1241-1246 (1957). This Smith paper also describes the polymerization of such epoxides and the use of the polymers as low load lubricants. None of these publications uses $SO_3$, and none mentions the preparation of bis(perfluoroalkyl)ethylene halohydrins or epoxides.

It is an object of this invention to provide novel halosulfonates and sulfates useful as intermediates in the production of mono- and bis(perfluoroalkyl)ethylene halohydrins and epoxides, and to provide novel bis(perfluoroalkyl)ethylene halohydrins and epoxides. It is a further object of this invention to provide an easy and inexpensive process for the preparation of mono(perfluoroalkyl)ethylene and novel bis(perfluoroalkyl)ethylene halohydrins and epoxides, and the intermediate sulfates and halosulfonates, by the reaction of mono- and bis(perfluoroalkyl)ethylenes with $SO_3$ and a halogen, and other subsequent reactions to produce the desired products. Mono- and bis(perfluoroalkyl)ethylene epoxides are useful as chemical intermediates and monomers.

SUMMARY OF THE INVENTION

This invention concerns novel (poly)sulfate and halosulfonate compounds of the formula

wherein each $R^2$ and $R^3$ is independently fluorine or perfluoroalkyl, $R^1$ is H or $-CFR^2R^3$, X is chlorine, bromine or iodine, and Z is selected from the group consisting of chlorine, bromine and $-OCHR^1CHXCFR^2R^3$, and n is an integer from 1 to 6.

This invention further concerns halohydrins of the formula

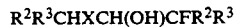

wherein $R^2$, $R^3$ and X are as defined above and epoxides of the formula

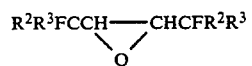

wherein $R^2$ and $R^3$ are defined as above. Also provided is a process for the production of fluorinated sulfates and halosulfonates comprising reacting $SO_3$ and a halogen selected from the group consisting of chlorine, bromine and iodine with a (perfluoroalkyl)ethylene of the formula $R^2R^3FCCH=CHR^1$, wherein $R^1$, $R^2$ and $R^3$ are as defined above. The halohydrins, sulfates and halosulfonates are useful as intermediates for the preparation of fluorinated epoxides, which in turn are useful as chemical intermediates and monomers.

DETAILS OF THE INVENTION

This invention concerns (poly)sulfates and halosulfonate compounds of the formula

wherein each $R^2$ and $R^3$ is independently fluorine or perfluoroalkyl, $R^1$ is H or $-CFR^2R^3$, X is chlorine, bromine or iodine, and Z is selected from the group consisting of chlorine, bromine and $-OCHR^1CHXCFR^2R^3$, and n is an integer from 1 to 6. Such sulfates and halosulfonates are made by the reaction of $SO_3$ and halogen (excluding fluorine) with (perfluoroalkyl)ethylenes (infra) of the formula $R^2R^3FCCH=CHR^1$ wherein $R^1$, $R^2$ and $R^3$ are as defined above. The sulfates and halosulfonates are useful as intermediates in the synthesis of the corresponding epoxides. It is preferred that n is 2 to 4. It is also preferred when $R^2$ is fluorine, and especially preferred when $R^2$ is fluorine and $R^3$ is n-perfluoroalkyl. It is most preferred that when $R^2$ is fluorine, $R^3$ is n-perfluoroalkyl and $R^1$ is either hydrogen or $-CF_2R^4$ wherein $R^4$ is n-perfluoroalkyl. It is also preferred that all perfluoroalkyl groups individually contain up to 12 carbon atoms each. In preferred compounds Z and X are chlorine and bromine, and in especially preferred compounds Z and X are chlorine. In another preferred compound Z is —OCHR$^1$CHXCFR$^2$R$^3$.

By the term "perfluoroalkyl" (including "n-perfluoroalkyl") herein is included a perfluoroalkyl group in which up to 2 fluorine atoms may be substituted by hydrogen and/or chlorine. Perfluoroalkyl groups also include branched structures and may contain ether oxygens between alkyl segments.

This invention further concerns halohydrins of the formula

wherein R$^2$, R$^3$ and X are as defined above. It is preferred when each R$^2$ is fluorine, and especially preferred when each R$^2$ is fluorine and each R$^3$ is n-perfluoroalkyl. It is also preferred when all perfluoroalkyl groups individually contain up to 12 carbon atoms each. It is preferred when X is chlorine and bromine, and especially preferred when X is chlorine. Such halohydrins may be reacted with base to form epoxides, which are useful as chemical intermediates (infra).

This invention concerns epoxides of the formula

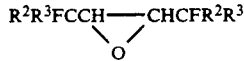

wherein each R$^2$ and each R$^3$ is independently fluorine or perfluoroalkyl. It is preferred when each R$^2$ is fluorine, and especially preferred when each R$^2$ is fluorine and each R$^3$ is n-perfluoroalkyl. It is also preferred when all perfluoroalkyl groups individually contain up to 12 carbon atoms each. Such epoxides are novel, and can be hydrolyzed to the corresponding glycol (see Experiment 2), which is useful as a monomer (see U.S. Pat. No. 3,337,644). Such epoxides are made by the reaction of the corresponding halohydrin (supra) with a base, as illustrated in the Examples. These reactions are analogous to those of halohydrins derived from mono(-perfluoroalkyl)ethylenes with bases; the latter reactions are well known to those skilled in the art.

It is obvious from the above discussion that in order to produce the above sulfates and halosulfonates it is necessary to react a mono- or bis(perfluoroalkyl)ethylene with SO$_3$ and a halogen. The halohydrins described above can be made by hydrolysis of the sulfates or halosulfonates derived from bis(perfluoroalkyl)ethylenes, while the epoxides can be made from the halohydrins by reaction with base. Thus, it is simpler to specify preferred species of the above compounds by the ethylene from which they were derived and in some cases the halogen used in the SO$_3$/halogen reaction with the ethylene. The chemistry of typical reactions, and the products obtained form them, are illustrated by the equations in the Examples.

Thus sulfates may be made from (perfluoro-n-butyl)ethylene, 1,2-bis(perfluoro-n-butyl)ethylene, 3,3,3-trifluoropropene (can also be called trifluoromethylethylene), 1,2-bis(trifluoromethyl)ethylene, (perfluorododecyl)ethylene, (6-H-perfluorohexyl)ethylene, (3-oxaperfluorohexyl)ethylene, (perfluoro-3-methylbutyl)ethylene, (3,6,9-trioxaperfluoro-5,8-dimethyldodecyl)ethylene, (3,4-dichloroperfluorobutyl)ethylene, (perfluoroethyl)ethylene, (1-trifluoromethyl-2-perfluoroethyl)ethylene, 1,2-bis(perfluoroethyl)ethylene and [1-perfluoroethyl-2-(2-H-tetrafluoroethyl)-]ethylene.

The halosulfonates may be made from chlorine and bromine and (perfluoro-n-butyl)ethylene, 1,2-bis(perfluoro-n-butyl)ethylene, 3,3,3-trifluoropropene [can also be called (trifluoromethyl)ethylene], 1,2-bis(trifluoromethyl)ethylene, (perfluorododecyl)ethylene, (6-H-perfluorohexyl)ethylene, (3-oxaperfluorohexyl)ethylene, (perfluoro-3-methylbutyl)ethylene, (3,6,9-trioxaperfluoro-5,8-dimethyldodecyl)ethylene, (3,4-dichloroperfluorobutyl)ethylene, (perfluoroethyl)ethylene, (1-trifluoromethyl-2-perfluoroethyl)ethylene, 1,2-bis(perfluoroethyl)ethylene and [1-perfluoroethyl)-2-(2'-tetrafluoroethyl]ethylene. Chlorine is a preferred halogen.

The halohydrins may be made from chlorine, bromine or iodine and 1,2-bis(perfluoro-n-butyl)ethylene, 1,2-bis(trifluoromethyl)ethylene and 1,2-bis(perfluoroethyl)ethylene. Chlorine and bromine are preferred halogens, and chlorine is especially preferred.

The epoxides may be derived from 1,2-bis(perfluoro-n-butyl)ethylene, 1,2-bis(trifluoromethyl)ethylene and 1,2-bis(perfluoroethyl)ethylene.

Preferred ethylenes used for the synthesis of the above sulfates, halosulfonates, halohydrins and epoxides (disubstituted ethylenes in the cases of the halohydrins and epoxides) are (trifluoromethyl)ethylene, 1,2-bis(trifluoromethyl)ethylene, (perfluoroethyl)-ethylene, 1,2-bis(perfluoroethyl)ethylene, (perfluorobutyl)ethylene and 1,2-bis(perfluorobutyl)ethylene.

A process for the production of fluorinated sulfates and/or halosulfonates comprises reacting SO$_3$ and a halogen selected from the group consisting of chlorine, bromine and iodine with a (perfluoroalkyl)ethylene of the formula R$^2$R$^3$FCCH=CHR$^1$, wherein R$^1$, R$^2$ and R$^3$ are as defined above. In preferred (perfluoroalkyl)ethylenes each R$^2$ is fluorine, and in especially preferred (perfluoroalkyl)ethylenes each R$^2$ is fluorine and each R$^3$ is n-perfluoroalkyl. In most preferred (perfluoroalkyl)ethylenes R$^2$ is fluorine, R$^3$ is n-perfluoroalkyl and R$^1$ is either hydrogen or —CF$_2$R$^3$, wherein R$^3$ is n-perfluoroalkyl. Preferred (perfluoroalkyl)ethylenes (those preferred above, or others) have perfluoroalkyl groups individually containing up to 12 carbon atoms.

The SO$_3$ used in the reaction may be added as a pure compound or dissolved in sulfuric acid, a solution commonly called oleum. Although no upper limit on the molar ratio of SO$_3$ to (perfluoroalkyl)ethylene is known, a preferred molar ratio of SO$_3$ to (perfluoroalkyl)ethylene is about 1.0 to about 10, especially preferred about 1.5 to about 5, most preferably about 3 to about 4. The effect of adding "excess" SO$_3$ on the value of "n" is discussed in connection with other fluorinated (poly)-sulfates in L. G. Anello and R. F. Sweeny, J. Org. Chem., Vol. 35, p. 120 (1970), which is hereby included by reference. It is believed the instant process is similarly affected by SO$_3$ levels.

The halogen used in the reaction is usually added as the pure halogen. Chlorine and bromine are preferred halogens, and chlorine is especially preferred. Depending on the physical form of the halogen, it may be added as a gas, liquid or solid. The molar ratio of halogen to (perfluoroalkyl)ethylene is about 0.25 to about 4, preferably about 0.5 to about 1.0. Although the ingredients may be mixed in any order, it is preferred to mix the SO$_3$ and halogen first, and then add the (perfluoroalkyl- )ethylene. Precautions should be taken to control the temperature while the reagents are mixed.

(Perfluoroalkyl)ethylenes useful in this process include, but are not limited to (perfluoro-n-butyl)ethylene, 1,2-bis(perfluoro-n-butyl)ethylene, 3,3,3-trifluoropropene (can also be called trifluoromethylethylene), 1,2-bis(trifluoromethyl)ethylene, (perfluorododecyl)ethylene, (6-H-perfluorohexyl)ethylene, (3-oxaperfluorohexyl)ethylene, (perfluoro-3-methylbutyl)ethylene, (3,6,9-trioxaperfluoro-5,8-dimethyldodecyl)ethylene, (3,4-dichloroperfluorobutyl)ethylene, (perfluoroethyl)ethylene, (1-trifluoromethyl-2-perfluoroethyl)ethylene, 1,2-bis(perfluoroethyl)ethylene and [1-perfluoroethyl-2-(2'-H-tetrafluoroethyl)]ethylene.

The reaction is run at about 0° C. to about 100° C., preferably about 15° C. to about 70° C. The reaction may require from about 10 min. to several hours, depending upon the reactants and temperature chosen. Pressure is not critical, although with a gaseous halogen such as chlorine, elevated pressures may be used to achieve higher temperatures and higher concentrations. Autogenous pressure, usually about 0.1 to about 100 atm. is often used. It is preferred to agitate the reaction mass during the reaction.

Although it is preferred to use no solvent, a solvent that is inert under reaction conditions may be used if desired.

The reaction vessel may be made of any material that is inert under the reaction conditions. Glass or Hastelloy ® (trademark of Stoody Deloro Stellite, Inc.) are suitable.

Starting materials should be reasonably dry, and moisture should be excluded during the reaction. It is sometimes convenient to use an inert atmosphere such as nitrogen or argon to exclude moisture.

The sulfate and halosulfonate product(s) of the reaction may be isolated by methods well known to those skilled in the art, such as crystallization or distillation. Alternatively, if "downstream" products are desired, the crude sulfates and halosulfonates may be hydrolyzed without isolation. Such methods are illustrated in the following Examples.

EXAMPLES

EXAMPLE 1

Reaction of (Perfluorobutyl)ethylene with $SO_3/I_2$

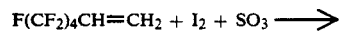

$$[F(CF_2)_4CHICH_2O]_2SO_2 + SO_2$$
$$1$$

Sulfur trioxide (9.6 g, 0.12 mol) was stirred at 25° C. while 32.1 g (0.13 mol) of (perfluorobutyl)ethylene was added. No indication of reaction was noted, so 30.5 g (0.12 mol) of iodine was added, whereupon an exotherm carried to 45° C. and then abated. The mixture was stirred overnight at 25° C., then at 50° C. for 30 min. Evolved gases were shown by IR analysis to be mainly $SO_2$. Removal of volatiles by warming at 0.15 mm gave 5.3 g of recovered olefin and some iodine. The solidified residue was broken up, stirred with water, filtered and air-dried to give 29.2 g (58% based on $SO_3$) of bis (3,3,4,4,5,5,6,6,6-nonafluoro-2-iodohexyl)sulfate (1), mp 45°–48° C. Recrystallization from methanol-water gave an analytical sample, mp 48°–51° C. IR ($CDCl_3$): 2984 and 2900 (sat'd CH), 1421 (possibly—$SO_2$—), 1250–1140 cm$^{-1}$ ($SO_2$, CF, C—O). NMR ($CDCl_3$): $^1$H and $^{19}$F spectra compatible with structure 1. Anal Calcd. for $C_{12}H_6F_{18}I_2O_4S$: C, 17.12; H, 0.72; I, 30.14; S, 3.81. Found: C, 17.21; H, 0.65; I, 29.98; S, 4.11

EXAMPLE 2

Reaction of (Perfluorobutyl)ethylene with $SO_3/I_2$

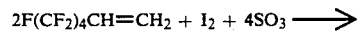

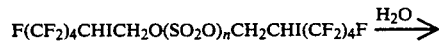

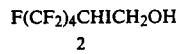

$$F(CF_2)_4CHICH_2OH$$
$$2$$

A mixture of 203 g (0.80 mol) of iodine and 394 g (1.6 mol) of (perfluorobutyl)ethylene was stirred while 250 g (3.125 mol) of $SO_3$ was added dropwise over 10 hr. Off-gases condensed in a −80° C. trap were warmed slowly to 25° C. while ca. 32 mL of $SO_2$ evaporated; residual liquid was returned to the reaction mixture, and the whole was stirred overnight. Volatiles were removed by warming to 50° C. at 2 mm, leaving a partly solid residue. The residue was stirred with a solution of 350 mL of conc. $H_2SO_4$ in 1 L. of water at 75°–80° C. for 5 hr. The mixture was cooled, filtered, and the organic layer of the filtrate was fractionated to give 163.2 g (26%) of 3,3,4,4,5,5,6,6,6-nonafluoro-2-iodohexanol-1(2), bp 56°–62° C. (3.5 mm), mp 30°–31° C. IR (neat): 3400 (OH), 2952 and 2896 (sat'd CH), 1250–1100 cm$^{-1}$ (CF,C—O). NMR ($CDCl_3$): $^1$H and $^{19}$F fit structure 2. Anal: Calcd. for $C_6H_4F_9IO$: C, 18.48; H, 1.03; I, 32.54. Found: C, 18.20; H, 0.94; I, 31.20, 31.05

EXAMPLE 3

Reaction of (Perfluorobutyl)ethylene with $SO_3/Br_2$

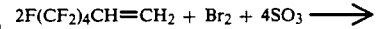

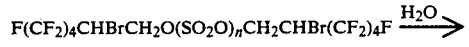

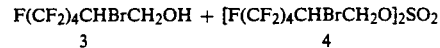

$$F(CF_2)_4CHBrCH_2OH + [F(CF_2)_4CHBrCH_2O]_2SO_2$$
$$3 \qquad\qquad 4$$

To a mixture of 32 g (16.7 mL, 0.4 mol) of sulfur trioxide and 16.0 g (0.10 mol) of bromine was added dropwise 49.2 g (0.20 mol) of (perfluorobutyl)ethylene. An exotherm and steady gas evolution subsided as the mixture was stirred after completion of the addition. Addition of another 16 g (0.10 mol) of bromine caused only a minor amount of further reaction. The mixture was stirred overnight and then evacuated at 20 mm to remove excess bromine. The stirred mixture was treated with 200 mL of water (cautiously at first), then heated at 80° C. for 13.5 hr. Fractionation gave 45.7 g (67%) of 3,3,4,4,5,5,6,6,6-nonafluoro-2-bromohexanol-1 (3), bp 64° C. (10 mm). IR (neat): 3401 (broad, OH), 2954 and 2898 (sat'd CH), 1250–1100 cm$^{-1}$ (CF, C—O). NMR ($CDCl_3$): $^1$H and $^{19}$F spectra fit the assigned structure. MS: spectrum of the compound and its trimethylsilyl derivative accord with structure 3.

Further fractionation gave 14.7 g (20%) of bis(3,3,4,4,5,5,6,6,6-nonafluoro-2-bromohexyl)sulfate (4), bp 98°–102° C. (0.02 mm). IR (neat): 2999 (sat'd CH), 1423 ($SO_2$), 1250–1100 cm$^{-1}$ (CF, C—O, $SO_2$). NMR ($CDCl_3$): $^1$H and $^{19}$F spectra fit the assigned

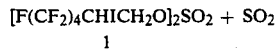

structure. Anal Calcd. for $C_{12}H_6Br_2F_{18}O_4S$: C, 19.27; H, 0.81; Br, 21.36; S, 4.29. Found: C, 19.22; H, 0.77; Br, 21.08; S, 4.72

EXAMPLE 4

Reaction of Bis(perfluorobutyl)ethylene with $SO_3/Br_2$

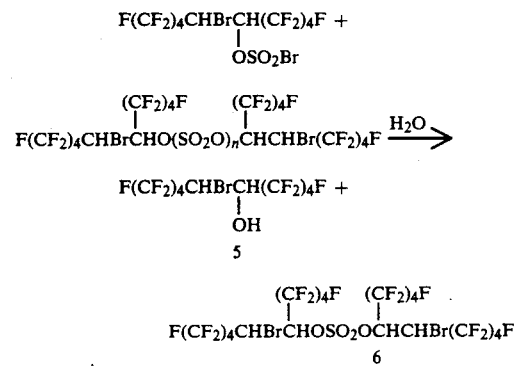

To a mixture of 16.0 g (0.10 mol) of bromine and 32.0 g (0.4 mol, 16.7 mL) of sulfur trioxide was added 46.4 g (0.10 mol) of 1,2-bis(perfluorobutyl)ethylene. The mixture was then stirred at 40°-50° C. for 2 hr. while gas evolution nearly ceased. After having stirred overnight at 25° C., the mixture was treated cautiously with 200 mL of water and stirred for 3 hr. Upon stirring overnight, the organic layer redeveloped a strong bromine color and the earliest GC product peaks grew while the next nearly disappeared; the latter product is presumed to be the bromosulfonate. The upper aqueous layer was extracted with 50 mL of $CH_2Cl_2$, the combined extract and product layer were washed with 50 mL of water, dried over $CaSO_4$, filtered and distilled. There was thus obtained 43.6 g. (78%) of perfluoro(6-bromo-5H,6H-decan-5-ol) (5), bp 80°-83° C. (9.5 mm). IR (neat): 3495 (broad, OH), 2996 (sat'd CH), 1250–1100 cm$^{-1}$ (CF, C—O). NMR (CDCl$_3$): $^1$H and $^{19}$F spectra are compatible with a mixture of 2 racemates of 5. MS: spectra of the product and of its trimethylsilyl derivative fit structure 5. Anal. Calcd. for $C_{10}H_3BrF_{18}O$: C, 21.41; H, 0.54; Br, 14.24. Found: C, 21.24; H, 0.54; Br, 13.93

The residue from the distillation was 96% pure 6, the sulfate of 5. IR (neat): 2986 (sat'd CH), 1433 (SO$_2$), 1250–1100 cm$^{-1}$ (CF, C—O, SO$_2$). NMR (CDCl$_3$): $^1$H and $^{19}$F are compatible with structure 6. MS: FAB+ gives the expected M+ peak.

EXAMPLE 5

Reaction of 3,3,3-Trifluoropropene with Oleum

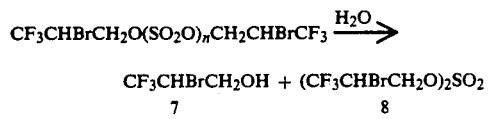

A mixture of 1036 g (2.6 mol on SO$_3$ basis) of 20% oleum and 80 g (0.50 mol) of bromine was stirred under a −80° C. condenser while 68 g (0.71 mol) of 3,3,3-trifluoropropene was passed in batchwise so as to keep the pot temperature at 9°-17° C. The addition required 4 hr., after which time the bromine color was nearly gone. The reaction mixture was extracted with 100 mL of small amount of sulfate 8 (identified by GC/MS and NMR) along with bromohydrin 7. The reaction mixture was then added dropwise to 2 L. of water, and the resulting mixture was extracted with 2×500 mL of $CH_2Cl_2$. Distillation of the combined extracts gave 47.7 g of 2-bromo-3,3,3-trifluoropropanol-1 (7), bp 60°-61° C. (50 mm). IR (neat): 3393 (OH), 2950 and 2894 (sat'd CH), 1250–1150 cm$^{-1}$ (CF, C—O). NMR (CDCl$_3$): $^1$H and $^{19}$F spectra fit bromohydrin 7. The aqueous acid mixture was heated at 90° C. for 30 min., cooled, and reextracted with 2×500 mL of $CH_2Cl_2$. Fractionation of these extracts afforded an additional 42.3 g of pure 7, bp 60°-62° C. (50 mm). The total yield of 7 was thus 90.0 g (66%).

EXAMPLE 6

Reaction of (Perfluorobutyl)ethylene with Oleum/Cl$_2$

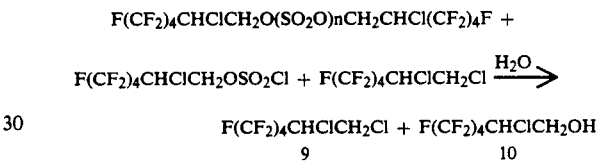

A portion of 20% oleum (200 g, ca. 0.5 mol of SO$_3$ present) was stirred under a −80° C. condenser while chlorine (35.5 g, 22 mL at −80° C., 0.5 mol) and (perfluorobutyl)ethylene (131 g, 0.50 mol) were added during 2 hr. portionwise and alternately in a manner to maintain some chlorine color and a pot temperature of 10°-15° C. The mixture was then stirred vigorously for 2 hr. while an exotherm to 37° C. occurred slowly and subsided. Analysis of the upper organic layer by GC/MS indicated the presence of both the sulfate and chlorosulfonate of chlorohydrin 10, in addition to 10 and dichloride 9. The entire mixture was added slowly and dichloride 9. The entire mixture was added slowly with stirring to 1 L. of water, and the whole was refluxed (75°-80° C.) for 1 hr. The organic layer was dried over MgSO$_4$, filtered and distilled to give 71.8 g (45%) of 1,2-dichloro-3,3,4,4,5,5,6,6,6-nonafluorohexane (9) bp 73°-79° C. (100 mm), followed by 38.0 g (25%) of 2-chloro-3,3,4,4,5,5,6,6,6-nonafluoro-hexanol-1 (10), bp 96°-97° C. (100 mm). IR (neat): 3387 (strong, OH), 2955 and 2899 (sat'd CH), 1250–1100 cm$^{-1}$ (CF, C—O). NMR (CDCl$_3$): $^1$H and $^{19}$F spectra are compatible with assigned structure. MS: spectra as is and of the trimethylsilyl derivative support structure 10. Anal. Calcd. for $C_6H_4ClF_9O$: C, 24.14; H, 1.35; Cl, 11.88. Found: C, 24.02; H, 1.37; Cl, 12.01.

EXPERIMENT 1

Reaction of an Iodohydrin with Base

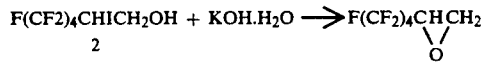

A mixture of 106 g (0.27 mol) of iodohydrin 2 and 25 mL of ether (to liquefy the iodohydrin) was added over a 30-min. period to 300 g (4.05 mol) of molten KOH.-H₂O which was being stirred at 150° C. The pot temperature rose to 160° C. and distillate was collected at bp 50°-90° C. After distillation had ceased, application of light vacuum gave a small additional amount of distillate. Volatile products were washed with 50 mL of water, dried over Mg SO₄, filtered and distilled to afford 48.4 g (68%) of (perfluorobutyl)oxirane (11), bp 46°-47° C. (100 mm), identified by G. C. and by comparison of the IR spectrum with that of a known sample, prepared by reaction of F(CF₂)₄CHBrCH₂OCOCH₃ with hot base.

Epoxide 11 was similarly produced by treatment of bromohydrin 3 and of chlorohydrin 10 with hot base.

EXAMPLE 7

Reaction of a Bromohydrin with Base

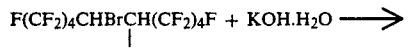

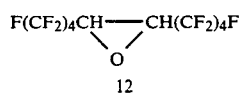

Bromohydrin 5 (65 g, 0.116 mol) was added dropwise but rather rapidly to 100 g (1.35 mol) of KOH.H₂O which was stirring at 140° C. under 25 mm pressure. Distillate was taken, bp 40°-70° C. (25 mm), while the pot temperature was kept at 140°-145° C., then raised to 155° C. (~10 mm) after addition had been completed. The crude product was washed with 50 mL of water, dried over MgSO₄, filtered and distilled to give 31.3 g (56% conv., 77% yield) of 2,3-bis(perfluorobutyl)oxirane (12), bp 60°-61° C. (25 mm). IR (neat): 3056 (sat'd. CH, weak), 1250-1100 cm⁻¹ (CF). NMR (CDCl₃): ¹H and ¹⁹F show a 77:13 ratio of epoxide 12 stereoisomers. MS fits the epoxide 12 structure, including the mass-measured M⁺. Anal Calcd. for C₁₀H₂F₁₈O: C, 25.02; H, 0.42. Found: C, 22.21, 22.52; H, 0.38, 0.36

The distillation residue was 17.5 g (27%) of recovered bromohydrin 5.

EXPERIMENT 2

Hydrolysis of an Epoxide

The following experiment demonstrates ring-opening of a 2,3-bis(perfluoroalkyl)ethylene oxide with trifluoromethanesulfonic acid to give the corresponding glycol monotrifluoromethanesulfonate. The latter provides the glycol on hydrolysis.

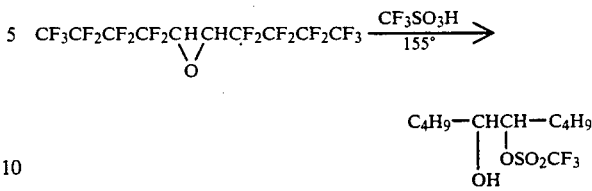

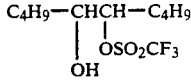

A homogeneous mixture of 19.0 g (0.040 mol) of 2,3-bis(perfluorobutyl)ethylene oxide and 17.7 g (0.118 mol) of trifluoromethanesulfonic acid was heated at 155° C. in a sealed heavy-walled tube for 40 hr. GC showed the epoxide had reacted to give a single product in about 30% conversion. Analysis by GC/MS confirmed the structure as monoester; m/e 611 (M⁺-F), 481 (M⁺-CF₃SO₂O). The trimethylsilyl derivative established the presence of one hydroxyl group; m/e 687 (M⁺-CH₃O).

Although preferred embodiments of the invention have been described hereinabove, it is to be understood that there is no attempt to limit the invention to the precise constructions herein disclosed, and it is to be further understood that the right is reserved to all changes coming within the scope of the invention as defined by the appended claims.

What is claimed is:

1. A halohydrin of the formula

R²R³CHXCH(OH)CFR²R³ wherein each R² and R³ is independently fluorine, perfluoroalkyl, or ether substituted perfluoroalkyl, and X is chlorine, bromine or iodine.

2. A halohydrin as recited in claim 1 wherein R² is fluorine.

3. A halohydrin as recited in claim 2 wherein R³ is n-perfluoroalkyl.

4. A halohydrin as recited in claim 1 wherein all perfluoroalkyl groups individually contain up to 12 carbon atoms each.

5. A halohydrin as recited in claim 3 wherein all perfluoroalkyl groups individually contain up to 12 carbon atoms each.

6. A halohydrin as recited in claim 1 wherein X is chlorine.

7. A halohydrin as recited in claim 3 wherein X is chlorine.

* * * * *